United States Patent [19]
Wenstrom, Jr.

[11] Patent Number: 5,814,051
[45] Date of Patent: Sep. 29, 1998

[54] SUTURE ANCHOR INSERTION SYSTEM

[75] Inventor: Richard F. Wenstrom, Jr., Norwood, Mass.

[73] Assignee: Mitex Surgical Products, Inc., Westwood, Mass.

[21] Appl. No.: 870,856

[22] Filed: Jun. 6, 1997

[51] Int. Cl.[6] ................................................ A61B 17/04
[52] U.S. Cl. ............................................ 606/104; 606/232
[58] Field of Search .................................. 606/104, 232, 606/72, 74, 75, 139

[56] References Cited

U.S. PATENT DOCUMENTS

| | | | |
|---|---|---|---|
| 4,946,468 | 8/1990 | Li | 606/232 |
| 5,002,550 | 3/1991 | Li | 606/139 |
| 5,078,730 | 1/1992 | Li et al. | 606/228 |
| 5,100,417 | 3/1992 | Cerier et al. | 606/139 |
| 5,174,087 | 12/1992 | Bruno | 53/430 |
| 5,258,016 | 11/1993 | DiPoto et al. | 606/232 |
| 5,411,506 | 5/1995 | Goble et al. | 606/104 |
| 5,522,844 | 6/1996 | Johnson | 606/232 |
| 5,522,845 | 6/1996 | Wenstrom, Jr. | 606/232 |
| 5,578,057 | 11/1996 | Wenstrom, Jr. | 606/232 |
| 5,584,860 | 12/1996 | Goble et al. | 606/104 |
| 5,683,401 | 11/1997 | Schmiedling et al. | 606/104 |

*Primary Examiner*—Gary Jackson
*Attorney, Agent, or Firm*—Nutter, McClennen & Fish, LLP

[57] ABSTRACT

A suture anchor insertion system includes a suture anchor installation tool having a handle, a retaining chamber formed integrally with the handle, and an elongate suture anchor inserting member. The system may also include a suture anchor releasably engaged on a distal end of the suture anchor inserting member, a packet at least partially disposed within the retaining chamber, and a suture thread having an intermediate portion attached to the suture anchor and two free ends stored within the packet.

24 Claims, 7 Drawing Sheets

FIG. 9A

SUTURE ANCHOR INSERTION SYSTEM

FIELD OF THE INVENTION

The invention relates to surgical systems for inserting a suture anchor into bodily tissue. More particularly, the invention relates to a suture anchor insertion tool which may be used to insert a suture anchor having a length of suture thread attached thereto.

BACKGROUND OF THE INVENTION

A variety of suture anchors for attaching suture to bone are known in the art. These anchors are often used to attach a length of suture thread to a bone in order to use the suture thread to attach soft tissue to the bone. Examples of suture anchors and suture anchor installation tools may be found in U.S. Pat. Nos. 4,898,156; 4,899,743; 4,946,468; 4,968,315; 5,002,550; 5,046,513; 5,192,303; 5,207,679; 5,217,486; 5,358,511; 5,411,506; 5,411,523; 5,520,696; 5,522,845 and 5,578,057.

Suture anchors typically have an anchor body, a suture attachment feature and a bone engaging feature for retaining the suture anchor within bone. The suture anchor may be inserted into a preformed hole in the bone, or with threaded (i.e., screw-type) suture anchors, the suture anchor may be screwed into the bone, with or without a preformed bore, in the manner of a common screw.

Suture anchor insertion tools known in the art for use with both types of suture anchors have drawbacks. These drawbacks include difficulty in handling small or "micro" suture anchors. It can be particularly difficult to retain small suture anchors on the tool until such time as they are inserted. Because of their small size, such "micro" suture anchors can be difficult to reattach to the insertion tool in a surgical environment if they do become prematurely separated from the tool.

Suture management during and after insertion of the anchor can be problematic as well. Smaller suture anchors, which are often pre-loaded onto the insertion tool and pre-threaded with suture thread, must be managed to ensure that the anchors and any attached suture thread and needles are properly delivered to the surgical site.

One known approach to suture management is to carry or thread the suture thread inside a cannulated suture anchor insertion tool, such as disclosed in U.S. Pat. Nos. 5,411,506 and 5,258,016. This approach is sometimes used with threaded suture anchors so that the suture thread may be managed even while twisting the insertion tool to insert the threaded anchor. In some instances, and particularly with smaller suture anchors, the suture anchor mating area on the distal portion of the insertion tool is so small that it is difficult to pass suture needles therethrough. Thus, if needles are required for post-anchor installation suturing procedures, it can be difficult to deliver the needles to the surgical site with the insertion tool. Other suture anchor insertion tools, such as the suture anchor insertion tool of U.S. Pat. No. 5,002,550, provide storage areas on the body of the tool. Such storage areas are closed off by a sliding cover that must be removed or opened to access the needles, thus requiring the surgeon to perform an extra step at the surgical site.

Other suture anchor installation tools manage suture thread attached to the anchor by equipping the installation tool with the external posts or surfaces, about which the suture thread is wound.

SUMMARY OF THE INVENTION

The present invention provides a system for inserting suture anchors. The system includes a suture anchor installation tool having a handle, an elongate suture anchor inserting member and a retaining chamber formed integrally with the handle.

The system may also include a suture anchor releasably mated to a distal end of the suture anchor inserting member. Suture anchors useful with the invention include threaded (i.e., screw-type) suture anchors and barbed (non-threaded) suture anchors. The system is particularly useful with extremely small suture anchors, sometimes referred to as "micro" anchors.

An intermediate portion of a length of suture thread may be secured to the suture anchor. The two free ends of the suture thread, and any needles preattached thereto, may be stored within a suture packet. The suture packet can be housed at least partially within the retaining chamber in the suture anchor installation tool. The packet can be retained within this chamber by a friction fit therein. The packet is releasable from the chamber in response to a predetermined tension placed on the suture thread, such as the tension that is applied when the suture anchor installation tool is separated from the suture anchor and removed from the surgical site after the suture anchor has been inserted into a bone.

In one embodiment, the suture anchor may be retained on the suture anchor inserting member, at least in part, by a tension placed on the suture thread that is attached to the anchor. In another embodiment, the suture anchor is releasably retained on the suture anchor inserting member by engaging deformable barbs on the anchor in openings provided on the suture anchor inserting member. An insertion pin, operable through an actuator on the handle of the insertion tool, is provided to release the barbed suture anchor and seat it within a bone.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
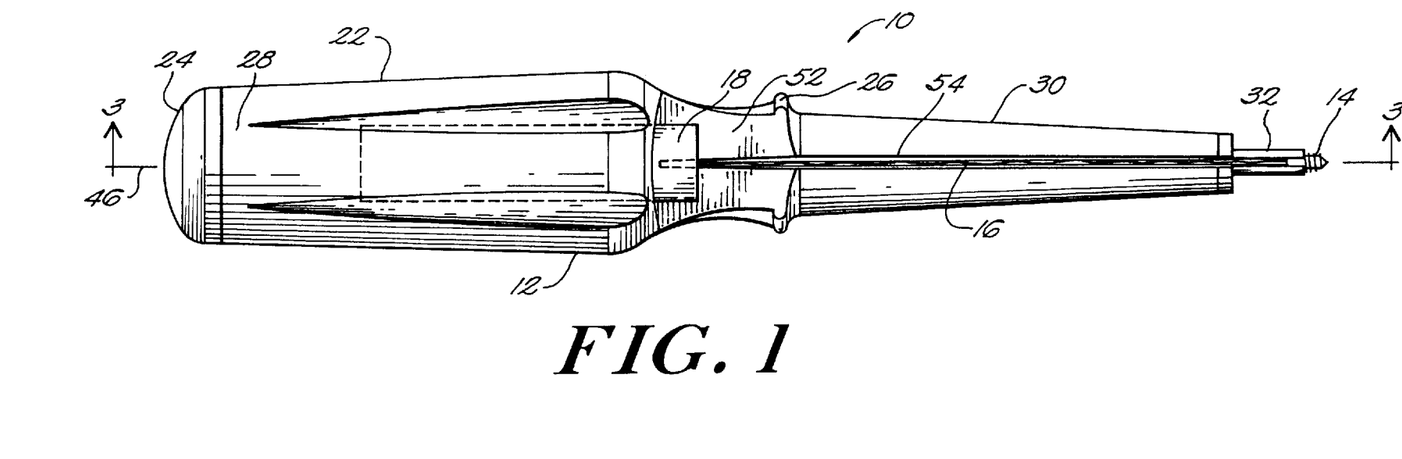
FIG. 1 is an elevated view of a suture anchor insertion system of the invention having a suture anchor insertion tool, a threaded suture anchor, suture thread and a suture thread and needle holding packet.
Figure 3:
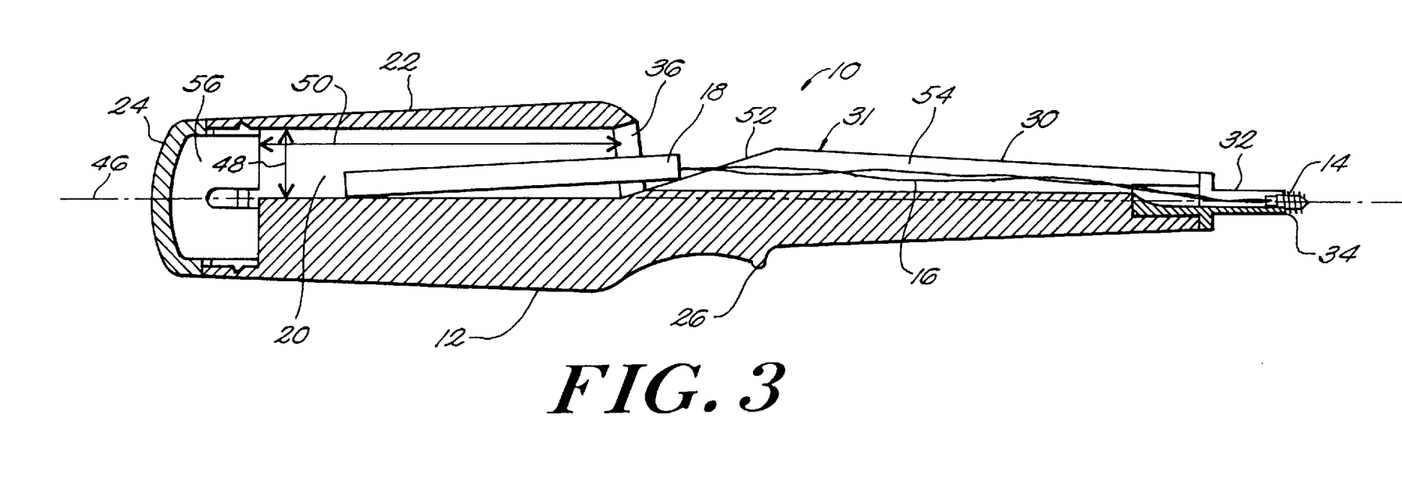
FIG. 3 is a cross-sectional view of the suture anchor insertion system of FIG. 1 taken along line 3—3.

A suture anchor insertion system 10 of the invention is illustrated in FIGS. 1 and 3. This exemplary system includes a suture anchor insertion tool 12, a suture anchor 14, at least one length of suture thread 16 and a packet 18 having at least suture thread carried therein. The packet 18 is at least partially inserted into a retaining chamber 20 formed within the suture anchor insertion tool 12.

Figure 2:
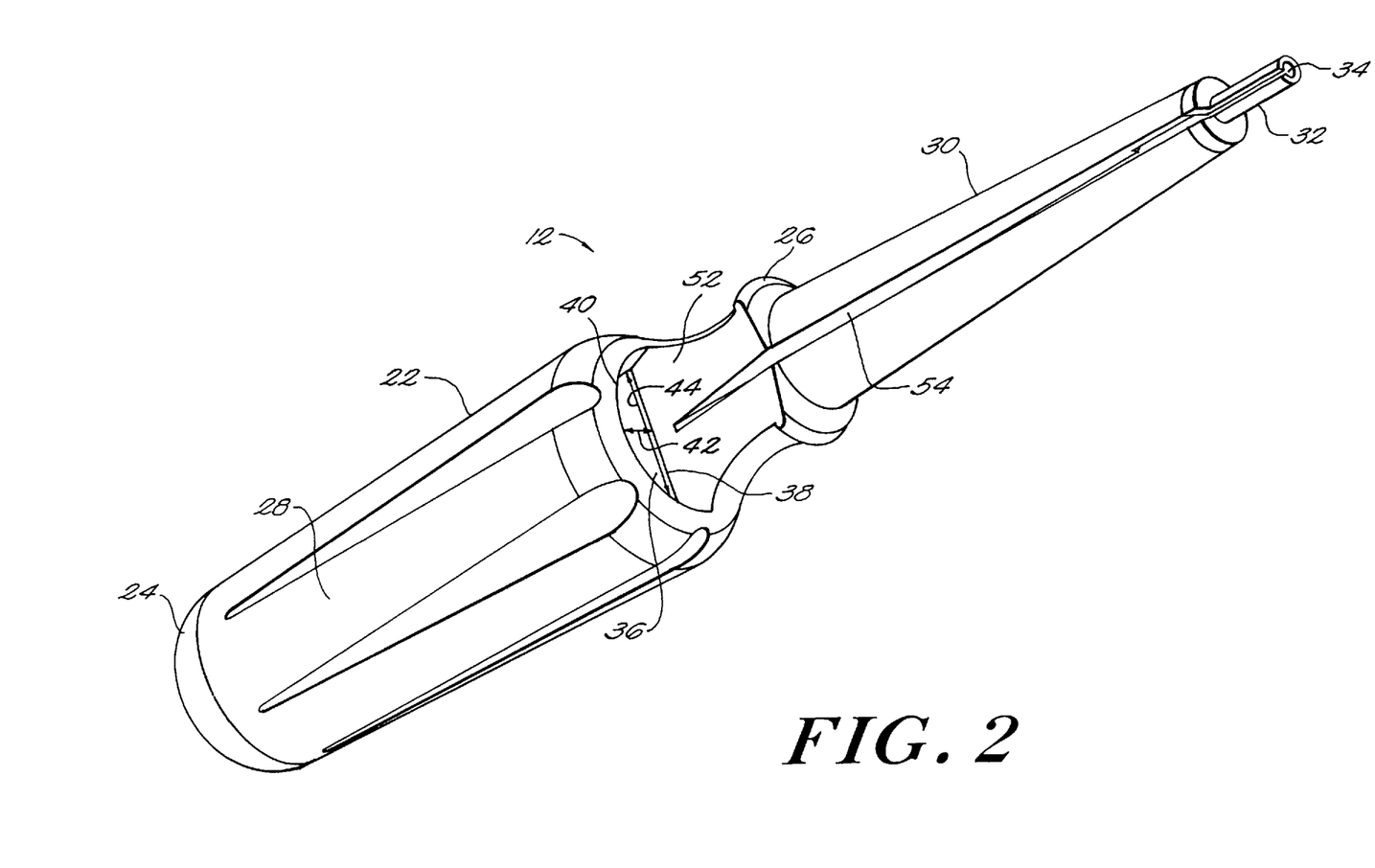
FIG. 2 is a perspective view of the suture anchor insertion tool of FIG. 1.

FIG. 2 illustrates the suture anchor insertion tool 12 having an elongate, generally cylindrical handle 22. The handle 22 has proximal 24 and distal 26 ends and a sidewall 28 disposed there-between. The handle 22 preferably is textured to allow a surgeon to grasp and manipulate the tool 12. Of course, the shape and dimensions of the handle 22 may be selected by a person of ordinary skill in the art to allow the handle 22 to be suitably grasped and manipulated by a surgeon in a surgical environment.

An elongate, generally cylindrical suture anchor inserting member 30 extends from the distal end 26 of the handle 22, and the inserting member 30 may be integral with the handle. The suture anchor inserting member 30 has a distal tip 32 that includes a suture anchor seating element 34. In one embodiment the suture anchor seating element may be in the form of a hexagonal opening. While the suture anchor installation tool 12 may be made from any material useful for constructing surgical tools, the distal tip 32 preferably is made of a durable metal, such as a stainless steel.

As noted above, the handle 22 includes an internal retaining chamber 20, which preferably is integral with the handle 22. As shown in FIGS. 2 and 3, the retaining chamber 20 has an opening 36 that faces substantially toward the distal end 26 of the handle 22. The opening 36 has one flat side 38, which is at an interior portion of the handle, and one arcuate side 40, which abuts sidewall 28. The height 42 of the opening 36 is generally in the range of approximately 0.125 to 0.500 inch, and preferably about 0.300 inch. The width 44 of the opening 36 is generally in the range of approximately 0.250 to 1.00 inch, and preferably about 0.600 inch. In practice, the size and shape of the opening 36, and the chamber 20, should be such that the packet 18 is retained by the force of a friction fit in the partially inserted position shown in FIG. 1. The force of the friction fit should be small enough, however, to allow the packet 18 to be pulled from the chamber 20 by a predetermined tension placed on the suture thread 16, such as the tension that is applied when the suture anchor insertion tool 12 is removed from the surgical site after the suture anchor 14 has been inserted into a bone.

As shown in FIG. 3, the retaining chamber 20 extends within the handle 22, proximally from the opening 36, to form a cavity that is substantially coaxial with a longitudinal axis 46 of the handle 22. The height 48 of the chamber 20 generally is in the range of approximately 0.125 to 0.500 inch, and preferably about 0.300 inch. The length 50 of the chamber is generally in the range of approximately 0.500 to 4.00 inches, and preferably about 2.00 inches. One of ordinary skill in the art will readily appreciate that modifications in the size of packet 18, chamber 20 and opening 36 may be made to accommodate insertion tools and/or suture packets of different sizes.

FIGS. 2 and 3 further illustrate that an angled barrier portion 52 is provided on a distal portion of the handle 22. The angled barrier portion 52 is a flat surface that originates at the flat side 38 of the opening 36 and extends distally to an interface surface 31 of the suture anchor inserting member 30 and the handle 22 at an angle so as to form a partial barrier between the opening 36 and the distal tip 32. The angle formed between the barrier portion 52 and the longitudinal axis 46 of the suture anchor insertion tool should be selected to achieve the desired friction fit between the packet 18 and the handle 22. The steeper the angle, the greater will be the force required to remove the packet 18 from the chamber 20. This angle may be between about 10° and 45°, preferably between about 15° and 20° and most preferably about 17°.

Referring still to FIG. 2, a slot 54 is provided on the suture anchor insertion tool 12. The slot 54 extends longitudinally from the suture anchor seating element 34 at the distal tip 32 of the suture anchor insertion member 30, through the length of the suture anchor insertion member 30 and into the angled barrier portion 52. The slot 54 should be of sufficient width and depth to seat two lengths of suture thread 16. Generally, the slot 54 has a width in the range of about 0.025 to 0.100 inch and a depth in the range of about 0.080 to 0.400 inch.

As shown in FIG. 3, the proximal portion 24 of the handle 22 may include a removable cap 56. Removal of the cap 56 facilitates access to the interior of the chamber 20 and to the packet 18 retained therein.

FIG. 3 illustrates the relationship between the various parts of the suture anchor insertion system of the invention. The suture anchor 14, which in this embodiment is a threaded suture anchor, is disposed on the suture seating element 34 on the distal tip 32 of the suture anchor insertion tool 12. An intermediate portion of suture thread 16 is attached to the suture anchor 14, leaving two lengths of the suture thread 16 to extend distally through the slot 54. The two lengths of the suture thread 16 extend into and are stored within the packet 18. The packet 18 is at least partially disposed within and is retained by the retaining chamber 20 in a frictional fit created by contact of the packet 18 with the chamber opening 36 and the angled barrier portion 52.

Figure 4:
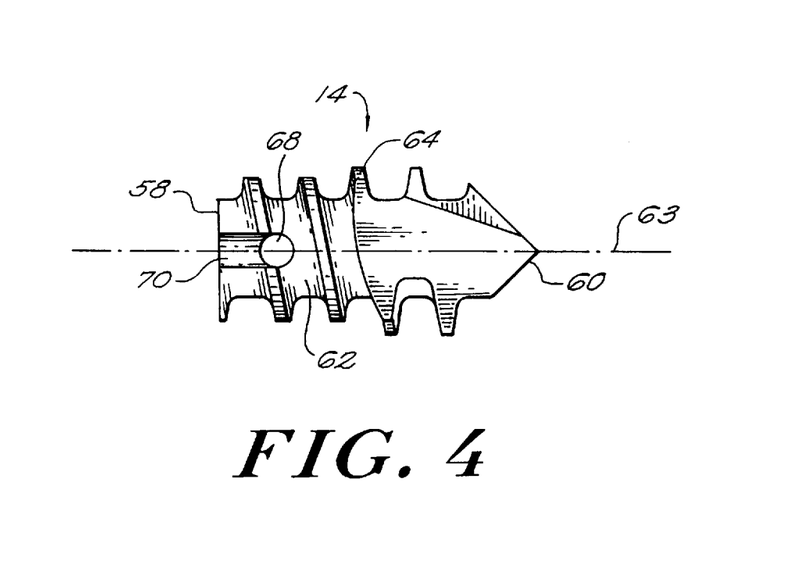
FIG. 4 is an elevated view, partially in section, of the threaded suture anchor of FIG. 1.
Figure 5:
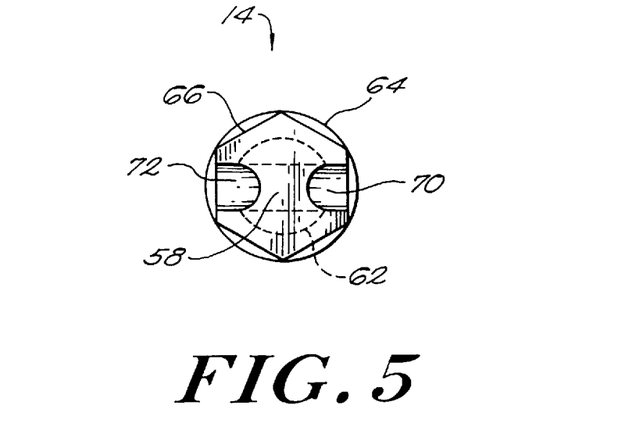
FIG. 5 is an end view of the threaded suture anchor of FIG. 4.

The threaded suture anchor 14, shown attached to the suture anchor installation tool in FIGS. 1 and 3, will now be described with reference to FIGS. 4 and 5. The exemplary threaded suture anchor 14 is substantially cylindrical and has a proximal end 58, an apex-forming distal end 60 and a sidewall 62 disposed between the proximal 58 and distal 60 ends. The distal end 60 may be self-tapping, or it may simply form an apex which may be threaded into a bore preformed within a bone. The threaded suture anchor 14 used with the system of the invention generally has a major diameter of less than about 0.090 inch. More preferably the major diameter of the anchor 14 is about 0.079 inch.

The sidewall 62 of the threaded suture anchor has at least one external thread 64 suitable for retaining the threaded suture anchor within a bone. The shape of the proximal-most portion of the threaded suture anchor 14 is configured to mate with the suture anchor seating element 34 on the distal tip 32 of the suture anchor inserting tool 12. In the exemplary threaded suture anchor 14, the proximal-most portion of the threaded suture anchor 14, including external threads on this portion, is in the form of a hexagon 66.

The threaded suture anchor 14 preferably includes a hole 68 that extends in a direction transverse to the longitudinal axis 63 of the anchor 14. The hole 68 is useful to seat an intermediate portion of the suture thread 16 when the anchor 14 is operatively attached to the suture anchor insertion tool 12. Grooves 70, 72 preferably communicate with the hole 68 and extend proximally therefrom. Grooves 70, 72 are useful to seat a length of suture thread, and should be of a sufficient width and depth to seat a length of suture thread while the suture anchor 14 is mated to the suture anchor seating element 34 of the suture anchor inserting tool 12. The width of the grooves 70, 72 is not otherwise particularly limited, but by way of example can be in the range of about 0.010 to 0.036 inch. Similarly, the grooves 70, 72 can be of virtually any depth as long as they are not so deep as to compromise the structural integrity of the threaded suture anchor 14. Preferably, the width of the anchor material remaining between the opposed grooves should be in the range of about 0.020 to 0.048 inches.

The suture anchor 14 may be retained to the suture anchor retaining element 34 on the distal tip 32 of the suture anchor installation tool 12 by a combination of the mating features of the element 34 and anchor 14, such as the hexagonal shape 66 of the proximal portion of the anchor 14, and tension from the suture thread 16 retained within the hole 68. As shown in FIGS. 1 and 3, the suture thread 16 is retained within the anchor 14, and extends proximally to the packet 18 where the suture thread 16 is stored. The packet 18 is held in place by a friction fit within the suture anchor insertion tool 12. Tension in the suture thread 16 can be adjusted by varying the placement of the packet 18 within the tool 12. This tension helps to retain the anchor 14 upon the anchor seating element 34.

Figure 6:
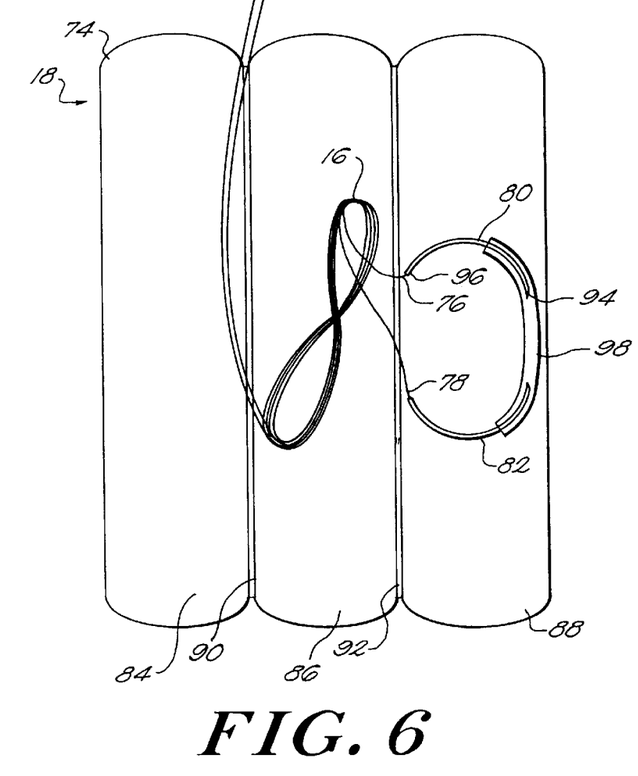
FIG. 6 is an elevated view of a suture thread and needle packet, in an open position, useful with the system of the invention.
Figure 6A:
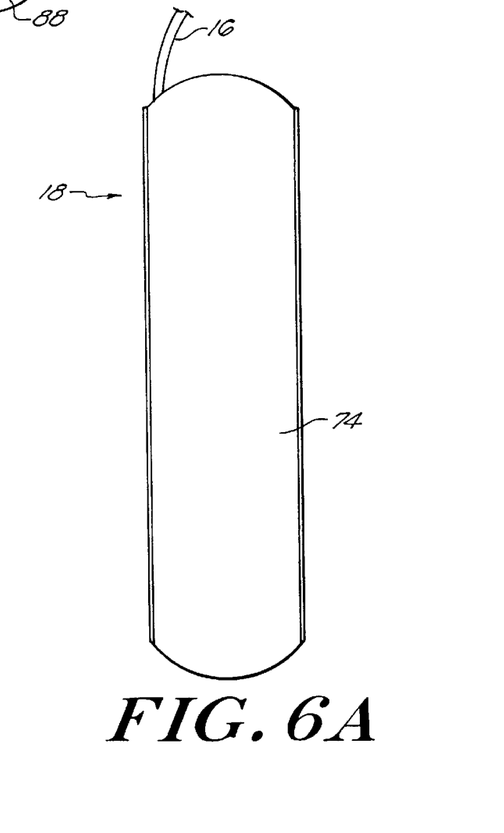
FIG. 6A is an elevated view of the packet of FIG. 6 in a closed position.

The packet 18, as shown in FIGS. 6 and 6A includes an outer wrapping member 74 which houses the suture thread 16 (which has two free ends 76, 78) and any needles 80, 82 attached thereto. In one embodiment the outer wrapping member 74 is divided into three portions 84, 86, 88, each of which is separated by creases 90, 92. As shown, the outer wrapping member 74 is laid flat in an "open" position. In use with the suture anchor installation system of the invention, the outer wrapping member 74 is folded along the two crease lines 90, 92 to enclose the suture thread 16 and needles 80, 82. This may be accomplished by folding portion 88 to cover portion 86, then folding portion 84 to cover portions 86 and 88. This results in the substantially rectangular packet 18 seen in FIG. 6A and FIGS. 1 and 3, which has two portions of suture thread 16 extending outward therefrom. Although not necessary, the internal portion of the wrapping member 74 may include a structure (not shown) for anchoring the thread and/or needles within the cover.

The packet 18 should be of dimensions suitable to fit snugly within chamber 20, while still being capable of easy removal in response to a predetermined tension placed on the suture thread 16, such as the tension that is applied when the suture anchor insertion tool 12 is removed from the surgical site after the suture anchor 14 has been inserted into a bone. For the closed packet 18 illustrated in FIG. 6A, the width of the packet 18 is generally in the range of approximately 0.250 to 1.00 inch, and preferably about 0.600 inch. The length of the packet 18 is generally in the range of approximately 1.00 to 4.00 inches. Of course, the dimensions of the packet 18 may vary depending upon the dimensions of the retaining chamber 20 and the opening 36.

The dimensions of the outer wrapping member 74 should be selected to achieve the appropriate closed packet 18 dimensions as described above. For the embodiment illustrated in FIG. 6, each of the three portions 84, 86, 88 should have length and width dimensions similar to the dimensions for the closed packet of FIG. 6A as described above. The overall width of the outer wrapping member 74 may therefore generally be in the range of approximately 0.250 to 1.00 inches. The length of the outer wrapping member 74 may generally be in the range of approximately 1.00 to 4.00 inches.

The outer wrapping member 74 may be constructed from among a variety of materials including paper-based material, such as cardboard, plastic and metal. A currently preferred material for the outer wrapping member 74 is nine point cardboard.

Alternative packets and packet materials may be used with the invention, provided that such alternative packets fit snugly within the chamber 20, are retainable within the chamber 20 by a frictional force, and are removable from the chamber 20 in response to a predetermined tension placed on the suture thread 16. Such alternative packets may include a packet constructed from a foam material, or a packet constructed from a soft plastic liner material that can be fastened or closed to form a packet.

One of ordinary skill in the art will appreciate that suture thread 16 may be constructed from a variety of suture materials. Exemplary materials include, but are not limited to, braided polyester and polydioxanone (PDS).

Each suture needle 80, 82 has a first tissue penetrating end 94 and a second trailing end 96. The size and shape of the needles used with the system of the invention may be selected by a person of ordinary skill in the art depending upon the specific application of the system, and in particular, depending upon whether the system is used in an open or closed (e.g. arthroscopic) surgical procedure. Generally, the needles 80, 82 are at least slightly curved. A needle holder 98 may optionally be provided. In one embodiment the needle holder 98 includes a length of tubing suitable to hold the penetrating end 94 of each needle 80, 82 within opposite sides of the tubing.

One of ordinary skill in the art will appreciate that the packet 18 may contain more than one type of needle attached to the suture thread, and may contain more than one suture thread attached to the suture anchor. Inclusion of multiple needles or threads within a packet allows a surgeon the most flexibility to accommodate the challenges of a given surgical procedure.

FIGS. 7 through 11 illustrate an additional embodiment of a suture anchor installation system of the invention.

Figure 7:
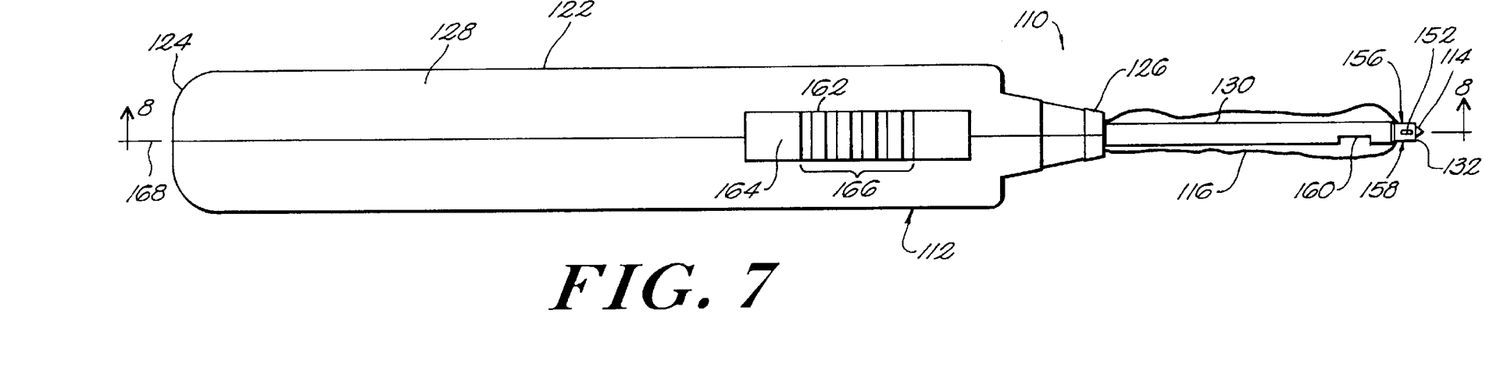
FIG. 7 is an elevated view of an additional embodiment of a suture anchor insertion system of the invention having a suture anchor insertion tool, a barbed suture anchor, suture thread and a suture thread and needle holding packet.
Figure 8:
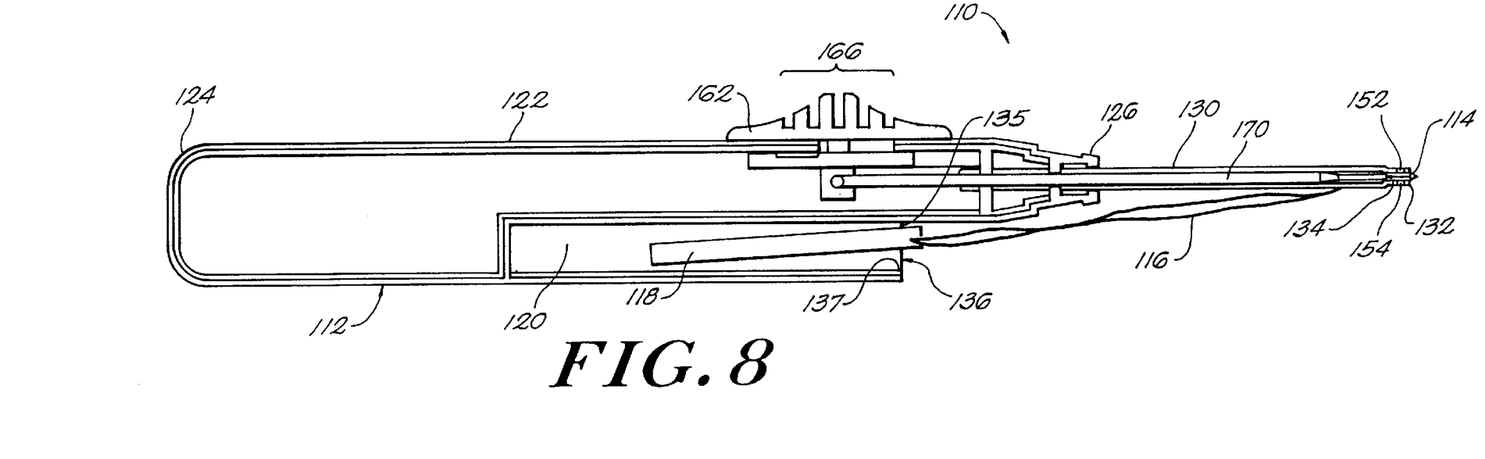
FIG. 8 is a cross-sectional view of the suture anchor insertion system of FIG. 7 taken along line 8—8.

FIG. 7 illustrates a suture anchor installation system 110 having a suture anchor installation tool 112 and a suture anchor 114 releasably mated to the tool 112. The cross-sectional view of FIG. 8 illustrates the tool 112 and anchor 114, as well as suture thread 116 attached to the suture anchor 114 and a packet 118 containing additional lengths of the suture thread 116 and any needles attached thereto. The packet 118 is at least partially housed within the retaining chamber 120 of the suture anchor installation tool 112.

The suture anchor installation tool 112 has an elongate, generally cylindrical handle 122 having proximal 124 and distal ends 126 and a sidewall 128 disposed there-between. The shape and dimensions of the handle 122 may be selected and varied by a person of ordinary skill in the art to allow the handle 122 to be suitably grasped and manipulated by a surgeon in a surgical environment.

A hollow, elongate suture anchor inserting member 130 extends from, and may be integral with, the distal end 126 of the handle 122. The suture anchor inserting member has a distal end 132 that includes a suture seating element 134 configured to releasably mate with the suture anchor 114. The suture anchor inserting member may be constructed of a material useful for surgical applications. A preferred material is a biomedically compatible metal such as stainless steel.

The retaining chamber 120 preferably is integral with the handle 122 and may be similar to the chamber 20 described above with respect to FIGS. 1–3. The chamber 120 has an opening 136 that faces substantially toward the distal end 126 of the handle 122. The opening 136 has a flat side 135, and arcuate side 137. If the housing is not truly cylindrical, that is, if the housing has a hexagonal or octagonal shape approximating a cylinder, the arcuate shaped side will be similarly angled to approximate an arc. The dimensions of the opening 136 and the chamber 120 may be similar to those described with respect to FIGS. 1 to 3. In practice, the height and shape of the opening 136, and the chamber 120, should be such that the packet 118 is retained by the force of a friction fit in the partially inserted position shown in FIG. 8. The force of the friction fit should be small enough, however, to allow the packet 118 to be pulled from the chamber 120 by the level of tension placed on the suture thread 116 during the act of disengaging the tool 112 from the suture anchor 114 and removing the tool 112 from the surgical site once the anchor has been inserted into a bone. The packet 118 may be identical to the packet described above with respect to FIGS. 6 and 6A.

Figure 9:
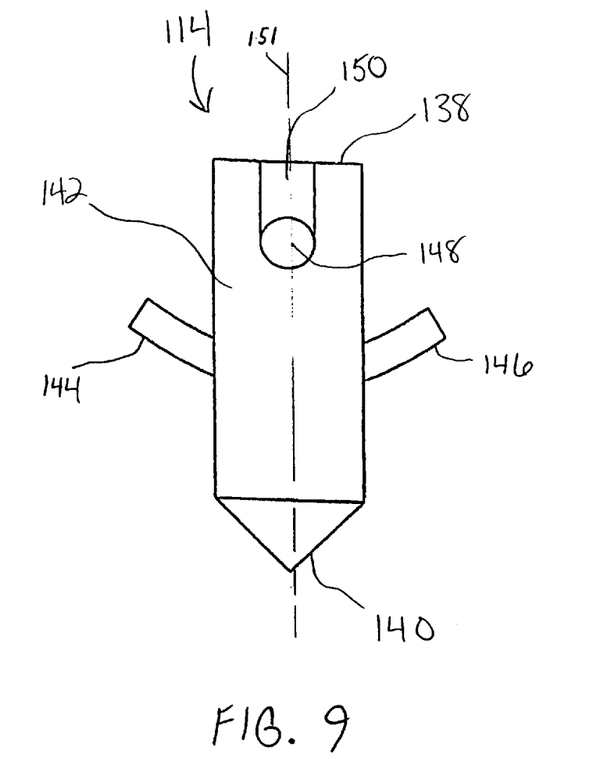
FIG. 9 is an elevated view of a barbed suture anchor useful with the suture insertion system of FIG. 7.

A suture anchor 114 useful with the system of FIGS. 7 and 8, illustrated in FIG. 9, includes a substantially cylindrical body with a proximal end 138, a distal end 140 forming an apex and a sidewall 142 disposed between the proximal 138 and distal 140 ends. The suture anchor 114 also has two opposed deformable barbs 144, 146 extending from the sidewall 142. The free ends of the deformable barbs 144, 146 may extend outwardly from the sidewall 142 and proximally (toward the proximal end 138 of the suture anchor 114) such that each barb defines an angle that is between about 10° and 90° with respect to the sidewall 142. More or fewer deformable barbs may be provided as desired to ensure proper retention of the suture anchor 114 within a bone.

The suture anchor 114 further includes a hole 148 that extends in a direction that is transverse to the longitudinal axis 151 of anchor 114. The hole 148 is useful to seat and retain an intermediate portion of suture thread 116 during use of the suture anchor insertion system 110. Grooves 150, which are similar to grooves 70, 72, are also provided on the suture anchor 114. These grooves 150 communicate with the hole 148 and extend proximally therefrom.

When non-threaded suture anchors are used with the system of the invention, such as the barbed suture anchor 114, the non-threaded suture anchor generally has a diameter of less than about 0.060 inch. More preferably the diameter of the non-threaded suture anchor is about 0.050 inch.

Figure 9A:
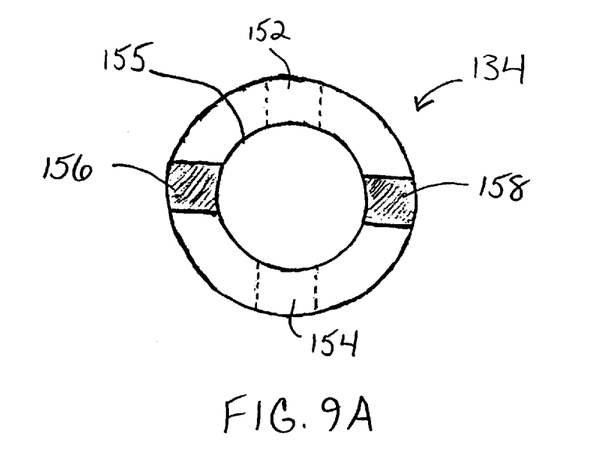
FIG. 9A is a distal view of the distal portion of the suture anchor insertion tool of FIG. 7.

The suture anchor seating element 134, as shown in the distal view of the suture anchor inserting member 130 in FIG. 9A, consists primarily of the inner bore 155 of the hollow suture anchor inserting member 130 and two opposed openings 152, 154 that help secure the anchor 114 to the inserting member 130. During assembly of the system 110, the anchor 114 is releasably mated to the suture anchor inserting member 130 by seating the barbs 144, 146 in the openings 152, 154.

Figure 10:
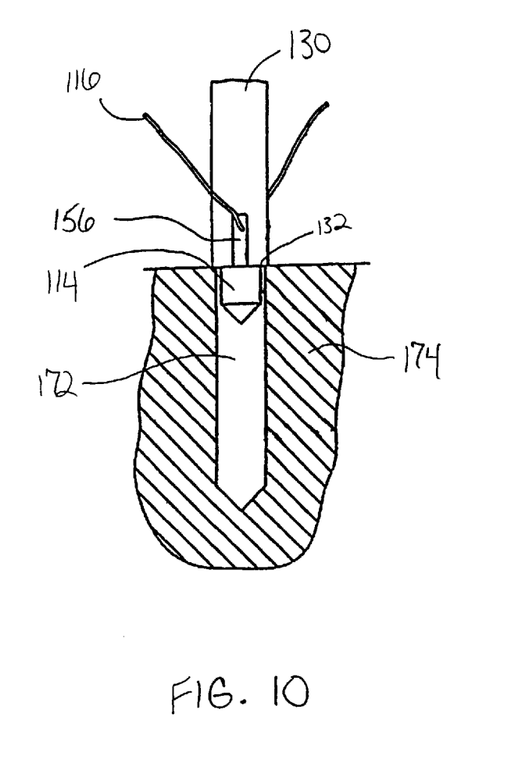
FIG. 10 is an elevated view of the distal portion of the suture anchor insertion system of FIG. 7, aligned with a preformed bore in a bone.

The suture seating element 134 of the suture anchor inserting member 130 may also include two opposed slots 156, 158. Slots 156, 158 are aligned with the hole 148 in the suture anchor 114. The slots 156, 158 provide clearance, as best shown in FIG. 10, in the suture anchor inserting member 130 for the suture thread 116 to exit from either side of the hole 150 in the suture anchor 114.

Referring again to FIGS. 7 and 8, the suture anchor inserting member 130 may also include a cut-out portion 160. The cut-out portion 160 provides access to the interior of the hollow suture anchor inserting member 130, thus allowing the suture anchor 114 to be inserted therein. During assembly of the system 110, the anchor 114 may be placed within the cut-out 160, then advanced toward the distal end 132. This action causes the barbs 144, 146 to deform until they are aligned with the holes 152, 154. Once aligned with holes 152, 154, the deformed barbs 144, 146 spring into the openings 152, 154 to releasably retain the suture anchor 114 within the suture anchor inserting member 130.

The handle 122 preferably includes an actuator 162 that is slidably mounted on the side wall 128 of the handle 122. The actuator may be in the form of a rectangularly-shaped base 164, having a series of flanges 166, with varying heights and angled surfaces, that allow the actuator 162 to be easily manipulated in either of two directions by a surgeon's thumb. The actuator may be manipulated to slide in a direction substantially parallel to the longitudinal axis 168 of the handle 122.

Figure 11:
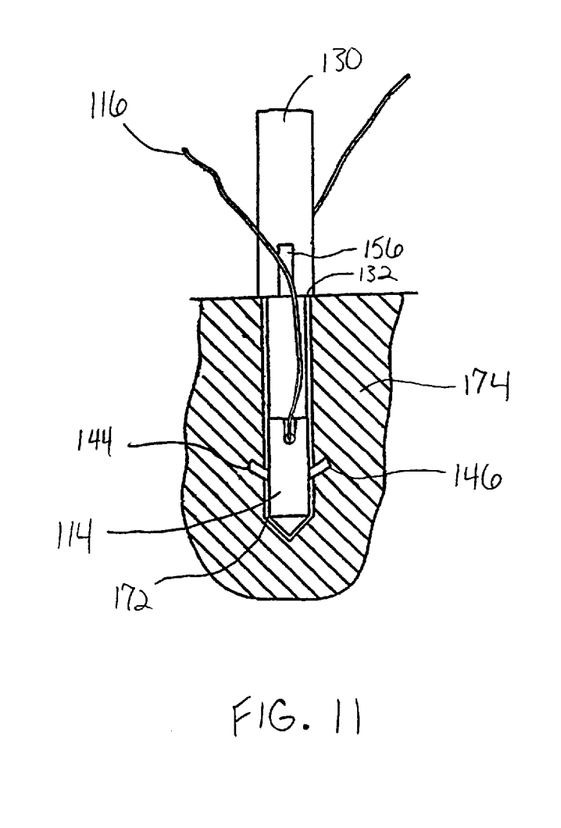
FIG. 11 is an elevated view of the distal portion of the suture anchor insertion system shown in FIG. 10 with the suture anchor inserted into the preformed bore in the bone.

The actuator 162 communicates with an insertion pin 170 that extends from the actuator 162, in the interior of the handle 122, through the interior of the hollow suture anchor inserting member 130 to communicate with the suture anchor 114. The operation of the insertion pin 170 is described with reference to FIGS. 10 and 11. First, the suture anchor 114, which is releasably secured to the distal end 132 of the suture anchor inserting member 130, is aligned with a preformed bore 172 in a bone 174, as illustrated in FIG. 10. As the actuator 162 is selectively moved from its proximal-most position toward its distal-most position, the insertion pin 170 contacts the suture anchor 114 and pushes the suture anchor 114 forward to free the barbs 144, 146 from the holes 152, 154. This action releases the suture anchor 114 from the suture anchor inserting member 130 and installs the suture anchor into the preformed bore 172 in the bone 174 as illustrated in FIG. 11.

Once the suture anchor 114 is securely installed within the bone 174, the suture anchor insertion tool 112 may be removed. Upon separation of the tool 112 and the anchor 114, and removal of the tool 112 from the patient's body, tension is applied by the suture thread (attached to the installed suture anchor), causing the packet 118 to be released from its frictional fit within the chamber 120. The packet 118 thus becomes separated from the suture anchor installation tool 112, and the suture thread 116 and any needles contained in the packet may be used by a surgeon.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A suture anchor insertion system, comprising:
    an elongate handle having a proximal end, a distal end and a side wall disposed between the proximal and distal ends;
    an elongate suture anchor inserting member extending from the distal end of the handle and having a suture anchor seating element at a distal end thereof, the suture seating element being effective to releasably seat a suture anchor; and
    a retaining chamber integral with the side wall of the handle, the retaining chamber having an opening facing substantially toward the distal end of the handle.

2. The system of claim 1, further comprising a suture anchor releasably seated in the suture anchor seating element.

3. The system of claim 2, further comprising a suture thread having two free ends and an intermediate portion, the intermediate portion being attached to a portion of the suture anchor.

4. The system of claim 3, further comprising at least one suture needle attached to a free end of the suture thread.

5. The system of claim 4, further comprising a packet disposed at least partially within the retaining chamber, the packet containing the at least one suture needle and the two free ends of the suture thread.

6. The system of claim 4, wherein the packet further includes a selection of suture needles and a selection of suture thread.

7. The system of claim 5, wherein the packet is releasable from the chamber when a predetermined tension is placed on the suture thread from the direction of the chamber opening.

8. The system of claim 5, further comprising:
    an actuator element slidably mounted on the sidewall of the handle; and
    an insertion pin, operatively connected to the actuator element and extending into the suture anchor inserting member, the insertion pin being operable by movement of the actuator element to release the suture anchor releasably seated in the suture anchor seating element.

9. The system of claim 1, wherein the retaining chamber extends proximately from the opening to form a cavity within the handle that is substantially coaxial with a longitudinal axis of the handle.

10. The system of claim 9, wherein the retaining chamber has a length in the range of about 0.5 to 4.0 inches.

11. The system of claim 9, wherein the retaining chamber has a height in the range of about 0.125 to 0.500 inches.

12. The system of claim 9, wherein the opening of the retaining chamber is substantially semi-circular in shape and has a height in the range of about 0.125 to 0.500 inch and a width in the range of about 0.250 to 1.000 inch.

13. The system of claim 2, wherein the suture anchor is selected from the group consisting of threaded suture anchors and non-threaded suture anchors.

14. The system of claim 13, wherein the suture anchor is a non-threaded suture anchor comprising a substantially cylindrical anchor member having a proximal end matable with the suture anchor seating element, a distal end, a side wall disposed between the proximal and distal ends and two opposed barbs extending from the side wall, the free end of each barb extending away from the anchor member and toward the proximal end of the anchor member such that each barb defines an angle with the sidewall of the anchor member that is between about 10° and 90°.

15. The system of claim 14, wherein the suture anchor inserting member further comprises a pair of openings, each being effective to engage one of the two opposed barbs to releasably retain the suture anchor upon the suture anchor inserting member.

16. The system of claim 13, wherein the suture anchor is a threaded suture anchor comprising a substantially cylindrical anchor member having a proximal end, a distal end, a side wall disposed between the proximal and distal ends and external threads disposed on at least a portion of the sidewall.

17. The system of claim 16, wherein the suture seating element is effective to releasably mount the threaded suture anchor upon the suture anchor inserting element to thread the threaded suture anchor into a bone, and to release the threaded suture anchor from the suture anchor inserting element upon exceeding a predetermined tensile force.

18. The system of claim 17, wherein an angled barrier portion is provided adjacent to the chamber opening and between the chamber opening and the suture anchor inserting member.

19. The system of claim 18, wherein a longitudinal slot is provided throughout the length of the suture insertion member and extending at least partially into the angled barrier portion, the slot being capable to seat at least one length of suture thread.

20. The system of claim 19, wherein the suture anchor seating element has a distal facing end that defines a hexagonal bore.

21. A suture anchor installation tool comprising:
    an elongate handle having a proximal end, a distal end and a side wall disposed between the proximal and distal ends;
    a hollow elongate suture anchor inserting member extending from the distal end of the handle and having a suture anchor seating element on a distal end thereof for releasably seating a suture anchor; and
    a retaining chamber extending into the handle and being substantially coaxial with the handle, the chamber having an opening facing the distal end of the handle.

22. The system of claim 21, further comprising:
    an actuator element slidably mounted on the sidewall of the handle;
    an insertion pin operatively connected to the actuator element and extending into the suture anchor inserting member such that movement of the actuator element effects the movement of the insertion pin to a position in which it effects a release of a suture anchor releasably seated in the suture anchor seating element.

23. The system of claim 22, wherein a longitudinal slot extends throughout the length of the suture insertion member and at least partially, the slot being effective to seat at least two lengths of suture thread.

24. The system of claim 23, wherein the suture anchor seating element includes a distal end that defines a hexagonal bore.

* * * * *